United States Patent
Shoemaker et al.

(10) Patent No.: US 8,420,072 B2
(45) Date of Patent: Apr. 16, 2013

(54) **VACCINATION OF SEX REVERSED HYBRID TILAPIA (*OREOCHROMIS NILOTICUS* X *O. AUREUS*) WITH AN INACTIVATED *VIBRIO VULNIFICUS* VACCINE**

(75) Inventors: Craig A. Shoemaker, Notasulga, AL (US); Benjamin R. LaFentz, Auburn, AL (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/071,193

(22) Filed: Mar. 24, 2011

(65) Prior Publication Data

US 2012/0244190 A1   Sep. 27, 2012

(51) Int. Cl.
*A01N 63/00* (2006.01)
*A61K 39/02* (2006.01)
*A61K 39/00* (2006.01)

(52) U.S. Cl.
USPC .................. 424/93.4; 424/234.1; 424/184.1; 424/817

(58) Field of Classification Search ............... None
See application file for complete search history.

(56) References Cited

U.S. PATENT DOCUMENTS 4,645,666 A * 2/1987 Manning et al. ........... 424/215.1
2007/0207165 A1 * 9/2007 Thiry et al. ................. 424/190.1

OTHER PUBLICATIONS

Park et al. Aquaculture 201: 187-197, 2001.*
Sanjaun et al. Appl. Environ. Microbiol. 75: 1604-1613, Mar. 2009.*

* cited by examiner

*Primary Examiner* — S. Devi
(74) *Attorney, Agent, or Firm* — John D. Fado; Evelyn M. Rabin; Gail E. Poulos

(57) ABSTRACT

*Vibrio vulnificus* can cause infections in aquaculture-raised fish and is considered an opportunistic human pathogen. We isolated *V. vulnificus* from diseased hybrid tilapia (Oreochromis niloticus X O. aureus) cultured in a North American water reuse aquaculture facility. We have characterized the isolate using biochemical and molecular methods, developed a disease infection model, and determined that formalin-inactivated whole-cell vaccine provides protection against *V. vulnificus*. The *V. vulnificus* isolate was determined to be biotype 1, 16S rRNA type B, vcg type C, and vvhA type 2. Fish vaccinated with the formalin-inactivated whole-cell vaccine responded to vaccination as measured by agglutinating antibody titer. In two separate trials, vaccinated tilapia exhibited relative percent survival of 73 and 60% following challenge with the homologous isolate. In additional trials, vaccinated tilapia exhibited survival values of up to 87.5% following challenge with a heterologous isolate. Use of a mineral oil adjuvant enhanced protection.

11 Claims, 3 Drawing Sheets

VACCINATION OF SEX REVERSED HYBRID TILAPIA (OREOCHROMIS NILOTICUS X O. AUREUS) WITH AN INACTIVATED VIBRIO VULNIFICUS VACCINE

BACKGROUND OF THE INVENTION

1. Field of the Invention

This invention relates to a novel vaccine against *Vibrio vulnificus*, an opportunistic pathogen of aquaculture-raised fish and also of humans.

2. Description of the Relevant Art

*Vibrio vulnificus* is a Gram-negative halophilic bacterium commonly associated with estuarine and marine environments worldwide (Strom and Paranjpye. 2000. Microbes and Infection 2:177-188). This pathogen has the ability to cause severe infections in humans following the consumption of raw seafood contaminated with *V. vulnificus*, and thus presents a food safety issue. Wound infections can also occur through exposure of open wounds to the bacterium (Jones and Oliver. 2009. *Infect. Immun.* 77:1723-1733).

In addition to being an opportunistic human pathogen, *V. vulnificus* can cause infections in economically important aquaculture-raised fish species. *V. vulnificus* infections in fish are most often associated with aquaculture-reared eels *Anguilla anguilla* and *A. japonica* (Fouz et al. 2006. *J. Fish Dis.* 29:285-291; Tison et al. 1982. *Appl. Environ. Microbiol.* 44: 640-646). However, there are also reports of this pathogen causing disease in pompano *Trachinotus ovatus* (Li et al. 2006. *Aquaculture* 261-17-25) and tilapia *Oreochromis* spp. under production conditions (Sakata and Hattori. 1988. *Fish Pathol.* 23:33-40; Chen et al. 2006. *J. World Aquacult. Soc.* 37: 82-88). *Vibrio vulnificus* was re-isolated from dead rainbow trout (*Oncorhynchus mykiss*) reared in marine production systems; however, the role of the bacterium in causing disease was uncertain (Pederson et al. 2008. *J. Fish Dis.* 31:659-667). Laboratory studies have demonstrated the susceptibility of other species, such as turbot *Psetta maxima*, sea bass *Dicentrachus labrax*, and rainbow trout (Biosca and Amaro. 1996. *Appl. Environ. Microbiol.* 62: 2331-2337; Fouz et al. 2002. *Aquacult* 212:21-30). With the ever increasing importance of cultured marine and freshwater fish as a source of protein, the potential for increased disease due to *Vibrio* spp. is recognized (Mlandineo and Miletic. 2008. *World Aquaculture Magazine* 39:26-29; Mahmud et al. 2010. *Appl. Environ. Microbiol.* 76: 4890-4895).

*V. vulnificus* exhibits a large degree of phenotypic and genotypic heterogeneity. Isolates can be classified into three biotypes based on biochemical characteristics (reviewed in Jones and Oliver, supra). However, although biochemical characteristics are commonly used to assign an isolate to a particular biotype, they are variable and may not be adequate for biotyping (Sanjuán et al. 2009. *Appl. Environ. Microbiol.* 75: 1604-1613). For example, biotype 1 isolates are commonly associated with human infection; however, isolates from any of the three biotypes have the potential to cause disease in humans. Most isolates that cause disease in fish have been reported as biotype 2 (Biosca and Amaro, supra; Fouz et al. 2002, supra; Fouz et al. 2010. *J. Fish Dis.* 33:383-390).

The genetic heterogeneity observed among *V. vulnificus* isolates has allowed for the development of molecular methods to characterize isolates and these have been useful to discriminate between isolates with human-pathogenic potential (i.e., clinical isolates) and environmental isolates. Three such methods include restriction fragment length polymorphism (RFLP) analysis of the 16S rRNA gene (Aznar et al. 1994. *Int. J. Systematic Bacteriol.* 44:330-337; Nilsson et al. 2003. *J. Clin. Microbiol.* 41:442-446), polymerase chain reaction (PCR) analysis of the hemolysin gene, vvhA (Senoh et al. 2005. *Microbiol. Immunol.* 49: 513-519), and PCR analysis of a virulence-correlated gene, vcg (Rosche et al. 2005. *Microbiol. Immunol.* 49: 381-389; Warner and Oliver. 2008. *Foodborne Path. Dis.* 5:691-693). Recently, Sanjuán et al. (supra) evaluated these three methods for their ability to distinguish between clinical and environmental isolates. Based on the results, the authors proposed three genotypic profiles: (1) vcg type C, 16S rRNA type B, and vvhA type 1, which included biotype 1 strains from human septicemia and oyster; (2) vcg type E, 16S rRNA type A, vvhA type 2, which included biotype 2 isolates and biotype 1 isolates from fish and water and some human isolates; and (3) vcg type E, 16S rRNA type AB, vvhA type 2, which included only biotype 3 isolates. However, in addition, they also reported atypical isolates which did not fall into these three genotypic profiles and concluded from their studies that no genotyping system was able to distinguish either clinical strains from environmental strains or biogroups within the species *V. vulnificus*, suggesting to them that new typing methodologies useful for public health had to be developed for this particular bacterial species.

Most literature has suggested that *V. vulnificus* isolates pathogenic to fish, including tilapia, are biotype 2 (Biosca and Amaro, supra; Fouz et al. 2002, supra; Fouz et al. 2010, supra). Laboratory studies in five species of fish (warm and cold-water) with four biotype 1 isolates supported this because infection with these isolates did not induce mortality in fish (Biosca and Amaro, supra). However, there are a few reports of *V. vulnificus* isolates, exhibiting similarities to biotype 1, causing disease in finfish. Sakata and Hattori (supra) isolated strains of *V. vulnificus* from diseased tilapia and suggested that they were similar to biotype 1 strains based on biochemical reactions. Chen et al. (supra) characterized *V. vulnificus* isolates from diseased tilapia in Taiwan and suggested that the isolates were similar to biotype 1 isolates based on 16S rRNA gene sequences, but these isolates produced unique biochemical reactions compared to other human clinical isolates. Li et al. (supra) characterized an isolate of *V. vulnificus* obtained from diseased pompano. Their isolate exhibited unique biochemical characteristics compared to all three biotypes, but 16S rRNA gene sequencing indicated that it was closely related to a biotype 1 isolate. Since definitive genotyping was not carried out on any of the aforementioned isolates of *V. vulnificus*, no further information on other identifying characteristics is available.

A recent study characterized *V. vulnificus* strains associated with tilapia aquaculture in Bangladesh and the results indicated that all the strains were biotype 1 and similar to human clinical isolates based on genotyping (Mahmud et al., supra). The authors hypothesized that environmental factors and aquaculture practices may contribute to the emergence of more virulent isolates (Mahmud et al., supra). The possibility of *V. vulnificus* (biotype 1 and human clinical genotype) emerging as a fish pathogen should not be overlooked as this may present a significant disease problem for aquaculture-reared fish species and an increased risk for food safety issues related to susceptible individuals handling and consuming raw fish harboring such isolates.

In the present study, we report on the isolation of *V. vulnificus* from diseased hybrid tilapia (*O. niloticus* X *O. aureus*) under production in a North American water reuse aquaculture facility. Given the facts that aquaculture of marine and freshwater fish has increased and that the increased numbers of cultured fish have become an important source of protein, there is a need to address the possibility of increased disease due to *Vibrio* spp. and there is a need to provide vaccines for protection against *Vibrio*-induced diseased fish.

SUMMARY OF THE INVENTION

We have now discovered a novel isolate of *Vibrio vulnificus* isolated from diseased tilapia and have designated the isolate, ARS-1 Br-09. Vaccines comprising the novel isolate are safe and effective for the control of *V. vulnificus* infections and provide acquired immunity against *V. vulnificus* in Nile tilapia (*Oreochromis niloticus*) and other fish.

In accordance with this discovery, it is an object of this invention to provide a novel, effective vaccine against *V. vulnificus*, comprising a novel *V. vulnificus* isolate effective for eliciting an immune response in fish which is protective against infection by virulent strains of *V. vulnificus* wherein said isolate of *V. vulnificus* is biotype 1, 16S rRNA type B, vcg type C, and vvhA type 2.

Another object of this invention is to provide an effective vaccine against *V. vulnificus* comprising a novel *V. vulnificus* isolate effective for eliciting an immune response in fish which is protective against infection by virulent strains of *V. vulnificus* wherein said isolate of *V. vulnificus* is ARS-1 Br-09 deposited under Accession Number NRRL-B-50360.

An additional object of this invention is to provide a formalin-inactivated *V. vulnificus* whole cell vaccine wherein the immunologically effective amount of a *V. vulnificus* isolate is formalin-inactivated NRRL-B-50360.

Another object of this invention is to provide an effective vaccine against *V. vulnificus* which may be administered by injection.

A further object of this invention is to provide a method of protecting fish against infection by virulent strains of *V. vulnificus* comprising administering to said fish the composition comprising a novel *V. vulnificus* isolate effective for eliciting an immune response in fish wherein said isolate of *V. vulnificus* is biotype 1, 16S rRNA type B, vcg type C, and vvhA type 2.

Yet another object of this invention is to provide a method of protecting fish against infection by virulent strains of *V. vulnificus* under conditions where fish are held in static salt water at concentrations of 1.5 g sea salt/L comprising administering to said fish the composition comprising a novel *V. vulnificus* isolate effective for eliciting an immune response in fish wherein said isolate of *V. vulnificus* is biotype 1, 16S rRNA type B, vcg type C, and vvhA type 2.

A further object of this invention is to provide a method of protecting fish against virulent strains of *V. vulnificus* wherein said virulent strains of *V. vulnificus* are homologous to the isolate of *V. vulnificus* having the identifying characteristics of biotype 1, 16S rRNA type B, vcg type C, and vvhA type 2.

An additional object of this invention is to provide a method of protecting fish against virulent strains of *V. vulnificus* wherein said virulent strains of *V. vulnificus* are heterologous to the isolate of *V. vulnificus* having the identifying characteristics of biotype 1, 16S rRNA type B, vcg type C, and vvhA type 2.

Another object of this invention is to provide a method of reducing bacterial loads of *V. vulnificus* in tilapia or other species in order to reduce the risk of humans acquiring infections from consumption of raw fish and/or wound infections resulting from handling fish harboring *V. vulnificus.*

A further object of this invention is to improve the viability and productivity of tilapia and other susceptible aquaculture species and to reduce economic losses in the aquaculture industry caused by *V. vulnificus.*

Other objects and advantages of the invention will become readily apparent from the ensuing description.

BRIEF DESCRIPTION OF THE DRAWINGS

FIGS. 1A and 1B depict restriction profiles of 16S rRNA gene amplified from four *Vibrio vulnificus* isolates digested with AluI (FIG. 1A) and HaeIII (FIG. 1B). Lane M: 50 bp DNA ladder; Lane 1: ARS-1 Br-09; Lane 2: CECT-529; Lane 3: CECT-4601; Lane 4: CECT-4608.

FIG. 2 depicts agarose gel electrophoresis of DNA products amplified from *Vibrio vulnificus* isolates by polymerase chain reaction (PCR) using the multiplex vcg primers. Lane M: DNA ladder; Lane 1: no template control; Lane 2: ARS-1 Br-09; Lane 3: CECT-529; Lane 4: CECT-4601; Lane 5: CECT-4608.

FIG. 3 depicts agarose gel electrophoresis of DNA products amplified from *Vibrio vulnificus* isolates by polymerase chain reaction (PCR) using the vvhA Type 1 primers (Lanes 1, 3, 5, 7, and 9) or vvhA Type 2 primers (Lanes 2, 4, 6, 8, and 10). Lanes M: DNA ladder; Lanes 1-2: no template control; Lanes 3-4: ARS-1 Br-09; Lanes 5-6: CECT-529; Lanes 7-8: CECT-4601; Lanes 9-10: CECT-4608.

DETAILED DESCRIPTION OF THE INVENTION

In the present study, *V. vulnificus* was isolated from hybrid tilapia experiencing a significant disease outbreak in a commercial water reuse aquaculture facility. The isolate designated ARS-1 Br-09 was characterized using biochemical and molecular methods. Biochemical characteristics indicated that the ARS-1 Br-09 isolate was biotype 1, similar to human clinical isolates. The molecular characterization of the isolate provided mixed results in regards to the ability to distinguish it as having human pathogenic potential. Genotyping the isolate using the 16S rRNA and vcg loci classified it as a clinical isolate; however, genotyping using the vvhA marker classified it as an environmental isolate. The isolate designated ARS-1 Br-09 is biotype 1, and its genetic profile is vcg type C, 16S rRNA type B, and vvhA type 2. Thus, the ARS-1 Br-09 isolate would be considered atypical according to the designations of Sanjuán et al. (supra).

The isolate recovered from the dead tilapia in our study produced limited disease in sex reversed hybrid tilapia using a freshwater infection model. However, if the infection was carried out in tanks containing static water and 1.5 g sea salt/L, mortality ranged from 60-93% and clinical signs of disease were noted (hemorrhaged skin and fins). The freshwater production facility, from which this isolate originated, had the practice of routinely adding salt to the system while purging the fish for transport to live markets. We hypothesize that over time the salinity increased in the system and may have been partly responsible for the disease outbreak. Alternatively, the bacterium may be similar to the isolate(s) recovered from the low saline- or freshwater-cultured tilapia in Taiwan (Chen et al., supra).

Most vaccine studies to date have focused on killed vaccines which protect against biotype 2 *V. vulnificus* isolated from eels (Collado et al. 2000. *Diseases Aquatic Organisms* 43:91-101; Esteve-Gassent et al. 2003. *Fish Shellfish Immunol.* 15:51-61). The bivalent vaccine produced for use in eels is based on two biotype 2 *V. vulnificus* isolates (Esteve-Gassent et al. 2004. *Fish Shellfish Immunol.* 16:93-105), both of which exhibit the 16S rRNA type A profile (Sanjuán et al., supra). There is a report in the literature of a vaccine developed for flounder (*Paralichthys olivaceus*) that utilized a human clinical isolate from Korea (Park et al. 2001. *Aquac-*

*ulture* 201:187-197). Unfortunately, the isolate was not molecularly characterized and no challenge data are presented in the results. The reported protective effect of the vaccine was inferred by in vitro immunological data, showing clearance of *V. vulnificus*. No work has been carried out on vaccine formulations against *V. vulnificus* in tilapia. Recent studies suggest *V. vulnificus* is emerging as an important pathogen of susceptible finfish aquaculture species (Mahmud et al., supra).

Results of the present study demonstrate that a formalin-inactivated vaccine against an atypical *V. vulnificus* isolate was capable of stimulating a humoral antibody response in sex reversed hybrid tilapia. Protective immunity based on relative percent survival was noted in the trials following intraperitoneal (IP) administration of the inactivated vaccine. Although a higher level of protection was seen in Trial 1 (See Example 4), this may be due to a 10 fold higher challenge dose used in Trial 2 (See Example 5) and/or the fact that the fish were held for a greater duration prior to challenge (78 days vs 40 days). Heterologous isolate challenge (See Example 6) using a *V. vulnificus* isolate obtained from a diseased eel (CECT 4601; biotype 2, 16S rRNA type A, vcg type E, and vvhA type 2) demonstrated that the inactivated vaccine of the invention based on the field isolate, biotype 1, vcg type C, 16S rRNA type B, and vvhA type 2, which was obtained from diseased tilapia, protected against the eel isolate (CECT 4601). In Trial 3 (See Example 6), protection was only observed when the inactivated vaccine was delivered with mineral oil adjuvant. In Trial 4 (See Example 6), however, both non-adjuvanted and adjuvanted vaccine formulations were effective and this may be a reflection of the overall challenge dose based on the fact that a lower dose ($5 \times 10^5$ CFU/fish) was given in Trial 4 as compared to $7 \times 10^5$ CFU/fish administered in Trial 3 (See Example 6). The vaccine of the invention can provide an effective means of preventing disease caused by biochemically and genetically diverse isolates of *V. vulnificus* in commercial tilapia production. Further, use of the vaccine can reduce bacterial loads of *V. vulnificus* in tilapia or other species and reduce the risk of humans acquiring infections from consumption of raw fish and/or wound infections resulting from handling fish harboring the bacteria.

"Vaccine" is defined herein in its broad sense to refer to any type of biological agent in an administrable form capable of stimulating a protective immune response in an animal inoculated with the vaccine. For purposes of this invention, the vaccine may comprise one or more formalin-inactivated *V. vulnificus* having the characteristic of the ARS-1 Br-09 isolate, i.e., biotype 1, vcg type C, 16S rRNA type B, and vvhA type 2.

Vaccination can be accomplished by injection, through oral ingestion or by means of aqueous immersion. The bacterial agent is inactivated with formalin and is prepared for administration by formulation in an effective immunization dosage with an acceptable carrier or diluent, such as water. The expressions "effective immunization dosage" and "immunologically effective amount or dosage" are defined herein as being that amount which will induce complete or partial immunity (elicit a protective immune response) in a treated fish against subsequent challenge by a virulent strain of *V. vulnificus*. Immunity is considered as having been induced in a population of fish when the level of protection for the population (evidenced by a decrease in the number of infected fish that die and/or a decrease in the severity of infection) is significantly higher than that of an unvaccinated control group (measured at a confidence level of at least 80%, preferably measured at a confidence level of 95%). The appropriate effective dosage can be readily determined by the practitioner skilled in the art by routine experimentation. One measure of protection following experimental challenge is relative percent survival (RPS) as described by Amend (1981. *Dev. Bio. Stand.* 49: 447-454) herein incorporated by reference. RPS is calculated according to the following formula:

$$RPS = 1 - \frac{\% \text{ vaccinate mortality}}{\% \text{ control mortality}} \times 100$$

A positive vaccine effect is indicated by a RPS equal to or greater than 60%. Typically, the vaccine is administered to 5-15 g fish by injection, oral delivery or any immersion device. Fish may be vaccinated with $1.5 \times 10^6$ to $2.8 \times 10^7$ CFU/fish of *V. vulnificus* by IP injection. CFU denotes colony forming units of *V. vulnificus*. The vaccine can be effectively administered any time after the fish attains immunocompetence, which for tilapia is at about two to fourteen days post-hatch. Other species of fish susceptible to *V. vulnificus* can be immunized after 21-30 days post-hatch or when they become immunocompetent to formalin-inactivated vaccine. Fish may also be vaccinated by immersion in water containing about $5 \times 10^5$ to about $1 \times 10^8$ CFU/mL of inactivated *V. vulnificus* for 10-30 min at a density of about 50 fish/L and a temperature of about 28° C. These parameters may be varied as desired such that a sufficient level of vaccination is acquired without induction of stressful conditions or loss of fish. Useable concentrations of *V. vulnificus* are considered to range from about $5 \times 10^5$ to about $1 \times 10^8$ CFU/ml of immersion medium. Useable vaccination times are seen to range from about 10 min to about 180 min, preferably from about 15 min to about 60 min. Temperature of the inoculation media may range within the physiologically acceptable limits of the fish involved, for tilapia preferably from about 25° C. to about 32° C., most preferably from about 25° C. to about 30° C. Concentrations of fish treated in the inoculation medium typically range from about 50 to about 100 fish/L, but, in the alternative, may be determined on a weight basis and range from about 0.5 to about 2.5 kg/L.

To produce large amounts of ARS-1Br-09 isolate for preparation of the vaccine, the bacterium may be cultivated under any conventional conditions and on media which promote growth of *V. vulnificus*. Without being limited thereto, the strain may be grown on a variety of solid or liquid media types, including but not limited to tryptic soy agar. In the alternative to growth on solid media, it is also envisioned that the strain may be grown in liquid culture. Without being limited thereto, conventional tryptic soy broth is preferred. The production of the vaccine in this manner may be conducted by stationary culture of the strain at 25-30° C. for 6-24 h. *V. vulnificus* were also grown in tryptic soy broth supplemented with 0.5% sodium chloride (TSB+NaCl) in 50 ml culture tubes at 28° C. for 6-24 h. All-vegetable based fermentation media are also preferred for use herein, as the use thereof eliminates the risks of the presence of animal products and infectious agents in the final vaccine product.

Following completion of the propagation, the resultant culture of *V. vulnificus* isolate ARS-1 Br-09 may be recovered for use as a vaccine. Cells, particularly those produced by liquid culture, may be optionally concentrated, for example, by centrifugation or filtration.

Cells were inactivated by adding 1% v/v formalin 18-24 h at 25° C. after determining the bacterial cell numbers by performing viable count; bacterial cell numbers may range from $1.5 \times 10^6$ to $2.8 \times 10^8$. Formalin-inactivated cells of the *V. vulnificus* isolate ARS-1 Br-09 are prepared for administration by formulation in an immunologically effective amount or dosage to the fish. The dose may further include pharmaceutically acceptable carriers and adjuvants known in the art. Depending on fish size, for an IP injection routine, a preferred dose in a fish would be about 0.1 mL ($1.5 \times 10^6$ to $2.8 \times 10^7$ CFU/fish). Although greater amounts of cells may be administered, use of such higher levels is generally considered impractical.

As noted above, the cells may be formulated in an optional, pharmaceutically acceptable carrier such as water, physiological saline, mineral oil, vegetable oils, aqueous sodium carboxymethyl cellulose, or aqueous polyvinylpyrrolidone. The vaccine formulations may also contain optional adjuvants, antibacterial agents or other pharmaceutically active agents as are conventional in the art. Without being limited thereto, suitable adjuvants include but are not limited to mineral oil, vegetable oils, alum, and Freund's incomplete adjuvant. Still other preferred adjuvants include microparticles or beads of biocompatible matrix materials. The microparticles may be composed of any biocompatible matrix materials as are conventional in the art, including but not limited to, agar and polyacrylate. The practitioner skilled in the art will recognize that other carriers or adjuvants may be used as well. For example, other adjuvants which may be used are described by Webb and Winkelstein (In: *Basic & Clinical Immunology*, 1984. Stites et al. (Eds.), Fifth Edition, Lange Medical Publications, Los Altos, Calif., pages 282-285), the contents of which are incorporated by reference herein.

The vaccines of the invention may be administered to the subject animal by any convenient route which enables the fish to elicit an immune response, such as by IP or intramuscular injection, bath immersion, oral administration, or nasal administration. However, IP injection or bath immersion is preferred for primary immunization, while oral immunization is preferred for secondary or booster immunization, when necessary. It is also envisioned that the surface of the fish may be punctured such as described by Nakanishi et al. (2002. Vaccine 20:3764-3769) or otherwise abraded or slightly descaled, prior to or during bath immersion, to facilitate exposure of the vaccine to the animal's immune system. The vaccine may be administered in a single dose or in a plurality of doses. Dependent upon rearing conditions, the vaccine may be administered in multiple doses, the timing of which may be readily determined by the skilled artisan.

IP injection of commercially available fish vaccines is commonly employed on fresh or marine aquaculture farms due to their reliability and high efficacy despite high cost per fish immunized and stress to the fish. Alternatively, vaccination against infection by *V. vulnificus* by bath immersion immunization offers several advantages. Among these advantages are lower cost per fish immunized, mass immunization of large numbers of fish, reduced stress, significantly higher rates of fish survival and the absence of adverse reactions to vaccination. Furthermore, bath immersion vaccination is an effective method for mass vaccination of smaller fish that cannot be injected or subjected to skin punctures.

EXAMPLES

Having now generally described this invention, the same will be better understood by reference to certain specific examples, which are included herein only to further illustrate the invention and are not intended to limit the scope of the invention as defined by the claims.

Example 1

Bacteria

Our laboratory was contacted in December 2009 by a North American hybrid tilapia producer experiencing a significant disease outbreak on a commercial water reuse aquaculture facility. Six dead fish were shipped to our laboratory and fish were necropsied using standard procedures. Aseptically acquired samples of the anterior kidney and brain were inoculated onto sheep blood agar (SBA) and incubated at 28° C. for 24-72 h. Both organs sampled from all six fish yielded pure cultures of a Gram-negative bacterium. The isolates were identified as *V. vulnificus* by fatty acid methyl ester analysis (Shoemaker et al. 2005. *J. Aquatic Animal Health* 17:267-274) and API 20E test (bioMérieux, Inc., Durham, N.C., USA). One isolate, ARS-1 Br-09 (deposited in the USDA Agricultural Research Service culture collection (NRRL) under accession number B-50360), was chosen for subsequent characterization and used in the infectivity and vaccine experiments.

Three additional *V. vulnificus* isolates (CECT 529 (ATCC 27562), CECT 4601 and CECT 4608) were included as positive controls in the characterization of the ARS-1 Br-09 isolate. These were cultured on SBA plates at 28° C.

Initial identification of isolate ARS-1 Br-09 as *V. vulnificus* was made by analysis of the fatty acid methyl ester profile using the microbial identification system that yielded a high percentage match (0.61 similarity index) in the rapid method RCLN50 data base (MIDI, Inc. 2002. In: *Sherlock Microbial Identification System Rapid Methods User's Guide, Version 5.0*. MIDI, Inc., Newark, Del.). The API 20 E test strip was used to biochemically characterize the *V. vulnificus* isolates in this study (Table 1). The profiles were 5146105 (ARS-1Br-09; CECT 4608), 5006005 (CECT 4601) and 5146005 (CECT 529).

TABLE 1

Biochemical profile and molecular characterization of *Vibrio vulnificus* isolated from the dead tilapia and from known culture collection isolates.

| Test | ARS-1Br-09 (Biotype 1 from tilapia) | CECT 529[1] (Biotype 1 from human) | CECT4601 (Biotype 2 from eel) | CECT4608 (Biotype 1 from eel) | Biotype3[2] |
|---|---|---|---|---|---|
| Oxidase | + | + | + | + | + |
| Arginine dihydrolase | − | − | − | − | − |
| Lysine decarboxylase | + | + | + | + | + |
| Sucrose fermentaion | − | − | − | − | − |
| Ornithine decarboxylase | + | + | − | + | + |
| Indole production | + | + | − | + | + |
| D-mannitol fermentation | + | − | − | + | − |

TABLE 1-continued

Biochemical profile and molecular characterization of *Vibrio vulnificus* isolated from the dead tilapia and from known culture collection isolates.

| Test | ARS-1Br-09 (Biotype 1 from tilapia) | CECT 529[1] (Biotype 1 from human) | CECT4601 (Biotype 2 from eel) | CECT4608 (Biotype 1 from eel) | Biotype3[2] |
|---|---|---|---|---|---|
| D-sorbitol fermentation | − | − | − | − | − |
| Citrate | − | − | − | − | − |
| ONPG | + | + | + | + | − |
| 16S rRNA Genotype | B[3] | A[3,4] | A[3,4] | B[3,4] | AB[4] |
| vcg genotype | C[3] | E[3,4] | E[3,4] | C[3,4] | E[4] |
| vvhA genotype | 2[3] | 2[3] | 2[3,4] | 1[3,4] | 1[4] |

[1]Type strain also referred to as ATCC 27562. Reference strains are sometimes variable for D-mannitol (Biosca et al. 1996. *Appl. Environ. Microbiol.* 62: 918-927).
[2]Results based on Bisharat et al. (1999. *The Lancet* 354: 1421-1424).
[3]Results from current study.
[4]Based on published literature (Sanjuán et al., supra).

Example 2

Molecular Characterization

Total DNA was extracted from *V. vulnificus* isolates using a DNeasy® Blood and Tissue kit (Qiagen, Valencia, Calif., USA) according to the manufacturer's protocol for Gram-negative bacteria. The 16S rRNA genotype of each isolate was determined as described by Nilsson et al. (supra), with minor modifications. A 492-bp segment of the 16S rRNA gene was amplified by PCR from each isolate using primers UFUL and URUL (Nilsson et al., supra; Avaniss-Aghajani et al. 1996. *J. Clin. Microbiol.* 34:98-102). PCR was performed using HotStarTaq® Plus Master Mix kit (Qiagen) and the final concentration of each component in the 20-µL reactions were as follows: 1× HotStarTaq Plus Master Mix, 0.3 µM each primer (UFUL, URUL), 1× CoralLoad Concentrate, and 50 ng total DNA. PCR amplification was performed with a Primus HTD thermocycler (MWG AG Biotech, Ebersberg, Germany) and the following cycling protocol was used: one cycle of 5 min at 95° C., 30 s at 57° C., 30 s at 72° C.; 30 cycles of 30 s at 94° C., 30 at 57° C., 30 s at 72° C.; final cycle of 30 s at 94° C., 30 s at 57° C., and 10 min at 72° C. PCR products from each isolate were separately digested with AluI and HaeIII (New England Biolabs, Ipswich, Mass., USA) restriction endonucleases according to the manufacturer's directions. Digested fragments were separated by agarose gel electrophoresis (2% w/v) in TAE buffer and stained with ethidium bromide. Isolates were ascribed to 16S rRNA genotype based on the size of DNA fragments obtained following digestion as described by Nilsson et al. (supra). Digestion of a 16S rRNA type A isolate (non-clinical) with AluI is predicted to produce DNA fragments of 248, 140, 62, and 42 by and fragments of 204, 168, and 120 by when digested with HaeIII. Digestion of a 16S rRNA type B isolate (clinical) with AluI is predicted to produce DNA fragments of 248, 202, and 42 by and fragments of 204, 147, 120, and 21 by when digested with HaeIII (Nilsson et al., supra).

Figure 1:
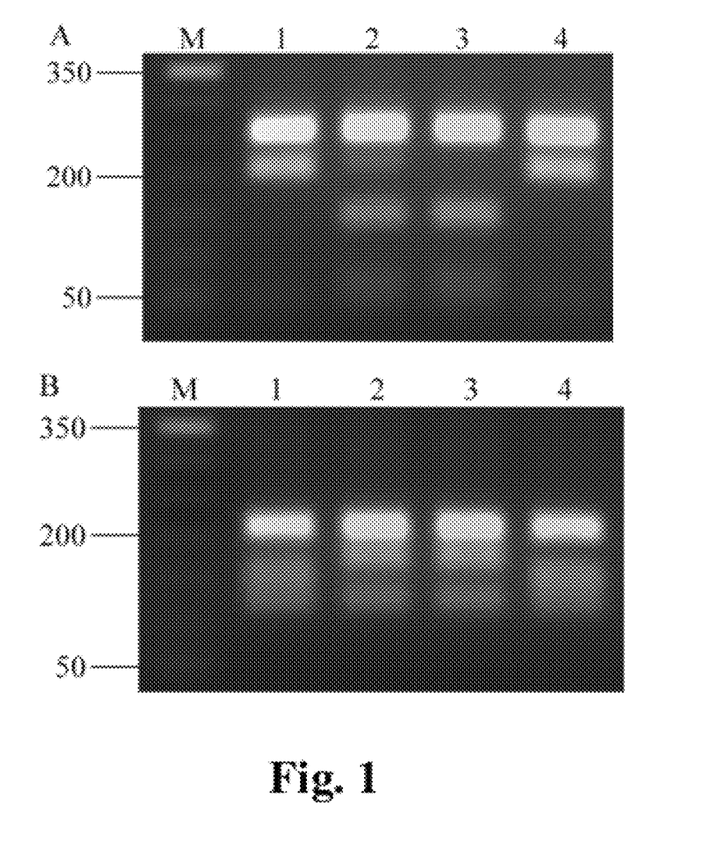

The results of the 16S rRNA genotyping demonstrated that ARS-1 Br-09 and CECT 4608 isolates were type B (clinical) and isolates CECT 529 and CECT 4601 were type A (environmental) (FIG. 1; Table 1).

The vcg (virulence-correlated gene) genotype of each isolate was determined by multiplex PCR as described by Warner and Oliver (supra), with minor modifications. PCR was performed using HotStarTaq® Plus Master Mix kit (Qiagen) and the final concentration of each component in the 20-µL reactions were as follows: 1× HotStarTaq Plus Master Mix, 0.1 µM each primer (vcgE F, vcgE R, vcgC F, vcgC R), 1× CoralLoad Concentrate, and 50 ng total DNA. PCR amplification was performed with a Primus HTD thermocycler (MWG AG Biotech) and the following cycling protocol was used: one cycle of 5 min at 95° C.; 30 cycles of 45 s at 94° C., 45 s at 55° C., and 45 s at 72° C.; final cycle of 10 min at 72° C. PCR products were separated by agarose gel electrophoresis (1.5% w/v) in TAE buffer and stained with ethidium bromide. Isolates were ascribed to vcg genotype based on the size of PCR product obtained following the multiplex PCR; a vcg type E isolate (environmental) is predicted to produce a 199 by product and a vcg type C isolate (clinical) is predicted produce a 97 by product (Warner and Oliver, supra).

Figure 2:
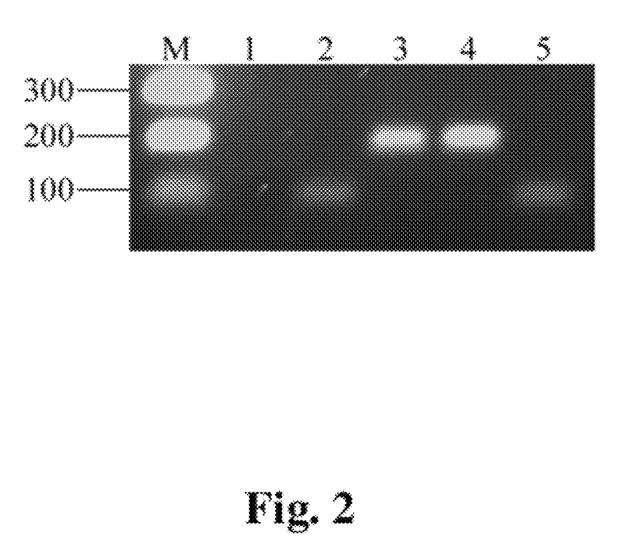

The results of the vcg genotyping demonstrated that ARS-1 Br-09 and CECT 4608 isolates were vcg type C (clinical) and isolates CECT 529 and CECT 4601 were vcg type E (environmental) (FIG. 2; Table 1).

The vvhA genotype of each isolate was determined by PCR as described by Senoh et al. (supra), with minor modifications. PCR was performed using HotStarTaq® Plus Master Mix kit (Qiagen) and the final concentration of each component in the 20-µL reactions were as follows: 1× HotStarTaq Plus Master Mix, 0.3 µM each primer (vvhA-1F and vvhA-1R; or vvhA-2F and vvhA-2R), 1× CoralLoad Concentrate, and 50 ng total DNA. PCR amplification was performed with a Primus HTD thermocycler (MWG AG Biotech) and the following cycling protocol was used: one cycle of 5 min at 95° C.; 30 cycles of 30 s at 95° C., 30 s at 57° C., and 90 s at 72° C.; final cycle of 10 min at 72° C. PCR products were separated by agarose gel electrophoresis (0.8% w/v) in TAE buffer and stained with ethidium bromide. Isolates were ascribed to vvhA genotype based on which primer pair resulted in amplification of the 813 by PCR product. The vvhA type 1 genotype is associated with clinical isolates and the vvhA type 2 genotype is associated with environmental isolates (Senoh et al., supra; Sanjuan et al., supra).

Figure 3:
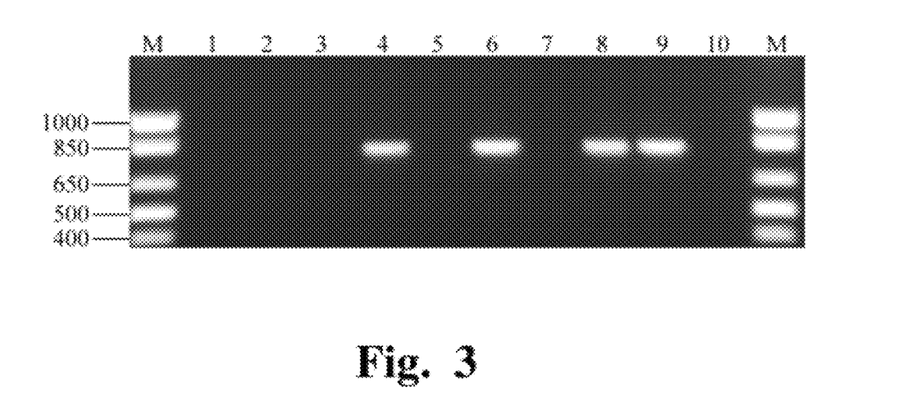

The results of vvhA genotyping demonstrated that isolates ARS-1 Br-09, CECT 4601, and CECT 529 were vvhA type 2 (environmental) and isolate CECT 4608 was vvhA type 1 (clinical) (FIG. 3; Table 1).

Example 3

Infectivity Trials with Hybrid Tilapia

Sex reversed hybrid tilapia (mean weight of 6.7 g) were obtained as fry from AQUASAFRA, Inc. (Bradenton, Fla., USA) and used as experimental animals. For trials 1 and 2, fish were stocked at approximately 50 fish in each of two 200 L aquarium at time of vaccination. For trials 3 and 4, four groups of 50 fish each were utilized (see vaccine and vaccination below for details). The fish were maintained in a flow through (0.5 L/min) system using de-chlorinated municipal water heated to 28±2° C. until challenge (see below).

Infectivity trials were conducted with 20-30 hybrid tilapia held in 57 L aquaria maintained on flow through freshwater at 28±2° C. Fish were intraperitoneally (IP) injected with $V.$ $vulnificus$ (ARS-1 Br-09) grown in tryptic soy broth supplemented with 0.5% sodium chloride (TSB+NaCl) in 50 ml culture tubes at 28° C. for 24 h. The doses administered ranged from $2.2 \times 10^6$ to $3.0 \times 10^7$ colony-forming units (CFU)/fish in four experiments. A fifth experiment consisted of IP injection at a dose of $2.0 \times 10^7$ CFU/fish using 31 hybrid tilapia. Fish in this experiment were injected after being maintained in 1.5 g sea salt/L water for 4 days prior to and for the duration of the infection (challenge) (7 days post injection).

Four separate experiments were conducted using flow through fresh water and IP inoculation. One of 20 fish died (5%) in 2 of the experiments; however, $V.$ $vulnificus$ was only recovered from one of the dead fish. No mortality was recorded in the other two experiments conducted in freshwater. In the fifth experiment where fish were maintained in 1.5 g sea salt/L water, 93% mortality was observed (29 of 31 fish died by day 7 post inoculation). Pure cultures of $V.$ $vulnificus$ were recovered from the fresh dead fish in the static salt water experiment.

Example 4

Vaccine and Vaccination—TRIAL 1

$Vibrio$ $vulnificus$ (ARS-1 Br-09) was grown at 28° C. in 500 ml TSB+NaCl for 24 h prior to adding 1% v/v formalin for 24 h at 25° C. to inactivate the cells. The formalin-inactivated whole cell vaccine was administered via IP injection of 100 μl per fish. Cell counts of a sample taken prior to inactivation indicated $1.5 \times 10^6$ CFU was given to each fish (n=50). Sham vaccinated fish received 100 μl of sterile TSB+NaCl (n=50).

At seventy eight days post vaccination (dpv), triplicate groups of 15 randomly selected fish from the treatment and control groups were allocated to six 57 L aquaria for the challenge. A single tank of 15 fish was included as mock infected controls. $Vibrio$ $vulnificus$ (ARS-1 Br-09) was grown in TSB+NaCl for 16 h at 28° C. and used for the challenge. Fish were challenged by IP injection with 100 μL containing $1.26 \times 10^7$ CFU and mock infected controls were IP injected with 100 μL of sterile TSB+NaCl. Following challenge, fish were held in the 57 L aquaria filled with static water containing 1.5 g sea salt/L water. Each day half of the tank water volume was drained, re-filled, and salt was added to maintain the concentration of sea salt at 1.5 g/L water. Microbial isolation of at least 50% of the dead fish from each tank was accomplished in all trials.

Vaccinated fish in Trial 1 had significantly ($p<0.05$) lower mortality than sham vaccinated fish following challenge (Table 2). Relative percent survival was 73%. Pure cultures of $V.$ $vulnificus$ were obtained from the brain of 18 of 18 dead sham vaccinated, challenged fish that were cultured. Nine of 9 dead vaccinated, challenged fish were also culture positive. There was no mortality in the mock infected control fish maintained under the same experimental conditions (Table 2).

TABLE 2

Mean cumulative percent mortality (CPM) and relative percent survival of inactivated $V.$ $vulnificus$-vaccinated, sex reversed hybrid tilapia challenged with the homologous $V.$ $vulnificus$ isolate (Trial 1).

| Treatment | N (replicate tanks of 15 fish each) | Mean CPM ± SE | Relative Percent Survival |
|---|---|---|---|
| Sham vaccinated challenged | 3 | $75.6 \pm 8.0^{a*}$ | — |
| Vibrio vulnificus vaccinated challenged | 3 | $20.0 \pm 3.9^b$ | 73 |
| Mock infected controls | 1 | 0.0 | NA |

*Means with different superscript letters were tested using the T-Test procedure of SAS and the results indicated that the variances were equal and the level of significance was $p < 0.05$.

In Trial 1, blood was collected from the caudal vasculature of 4 individual fish from each of the sham vaccinated and vaccinated fish prior to challenge using a non-heparinized syringe with 25-gauge needle to obtain serum for antibody titer determination. Following the challenge, blood was collected from the remaining fish in each aquarium to determine antibody titers post challenge. Serum was collected following centrifugation of clotted blood at 3000 g for 10 min. Agglutinating antibody titer against $V.$ $vulnificus$ was determined using a modified microagglutination method (Klesius et al. 2000. $Aquaculture$ 188:237-246). Briefly, $V.$ $vulnificus$ (ARS-1 Br-09) was grown for 8 h in TSB+0.5% NaCl at 28° C. and killed with 1% formalin (24 h at 25° C.). The cells were then centrifuged (5000 g) for 15 min and the resulting pellet was re-suspended and washed in phosphate buffered saline (PBS, pH 7.2). Following three washes, the bacteria were adjusted to an OD of 0.6 at 540 nm in PBS. Round bottom 96-well microtiter plates were initially plated with 25 μl of PBS. In each well of the first row, 25 μl of serum was added and mixed. Following mixing, two-fold serial dilutions were made. After this, 25 μl of the cell suspension was added to each well. Positive and negative control serum was included on each plate as assay controls. Plates were covered and incubated overnight (about 16 h) at 22±2° C. The agglutination endpoint was determined as the final dilution where cell agglutination was visible. Agglutination titers were reported as the reciprocal of the highest serum dilution showing visible agglutination.

Mean antibody titers were significantly higher ($p<0.05$) in the vaccinated fish (mean titer=56) at 78 days post vaccination as compared to the sham vaccinated fish (mean titer=5) in Trial 1 (Table 3). At twelve days post challenge a similar result was obtained where mean titers were significantly higher ($p<0.05$) in the vaccinated challenged fish (mean titer=206) as compared to the sham vaccinated challenged fish (mean titer=45) (Table 3).

TABLE 3

Agglutinating antibody titer post vaccination and post challenge with $Vibrio$ $vulnificus$ in sex reversed tilapia (Trial 1).

| Treatment | Day | Range of titers (N) | Mean titer* |
|---|---|---|---|
| Sham vaccinated | 78 post vaccination | 4-8 (4) | $5^a$ |
| Vaccinated | 78 post vaccination | 32-64 (4) | $56^b$ |
| Sham vaccinated | 12 post challenge | 16-128 (11) | $45^a$ |
| Vaccinated | 12 post challenge | 64-1024 (36) | $206^b$ |

*Means with different superscript letters at the same day are significantly different ($p < 0.05$).

Example 5

Vaccine and Vaccination—Trial 2

*Vibrio vulnificus* (ARS-1 Br-09) was grown in 500 ml TSB+NaCl for 8 h at 28° C. prior to adding 1% v/v formalin (18 h at 25° C.) to inactivate the bacteria. The formalin-inactivated whole cell vaccine was administered via IP injection of 100 μl per fish. Cell counts of a sample taken prior to the addition of the formalin indicated $2.8 \times 10^7$ CFU was injected per fish (n=57). Sham-vaccinated fish received 100 μl of sterile TSB+NaCl (n=55).

At forty dpv, triplicate groups of 15 randomly selected fish from the treatment and control groups were allocated to six 57 L aquaria for the challenge. A single tank of 15 fish was included as mock infected controls. *Vibrio vulnificus* (ARS-1 Br-09) was grown in TSB+NaCl for 6 h at 28° C. and used for the challenge. Fish were challenged and the water was maintained as described for Trial 1, with the exception that each fish received $2.15 \times 10^8$ CFU.

Similar results were obtained in Trial 2 with vaccinated fish showing significantly ($p<0.05$) lower mortality than sham-vaccinated fish following challenge (Table 4). Relative percent survival was 60%. Pure cultures of *V. vulnificus* were obtained from the brain of 30 of 30 sham vaccinated challenged fish that were cultured. Eleven of 11 dead vaccinated fish were also culture positive. There was no mortality in the mock infected control fish maintained under the same experimental conditions (Table 4).

TABLE 4

Mean cumulative percent mortality (CPM) and relative percent survival of inactivated *V. vulnificus*-vaccinated sex reversed hybrid tilapia challenged with the homologous *V. vulnificus* isolate (Trial 2).

| Treatment | N (replicate tanks of 15 fish each) | Mean CPM ± SE | Relative % Survival |
|---|---|---|---|
| Sham vaccinated challenged | 3 | $73.3 \pm 0.0^{a*}$ | — |
| Vibrio vulnificus vaccinated challenged | 3 | $28.9 \pm 4.4^{b}$ | 60 |
| Mock infected controls | 1 | 0.0 | NA |

*Means with different superscript letters were tested using the T-Test procedure of SAS and the results indicated that the variances were equal and the level of significance was $p < 0.05$.

Example 6

Vaccine and Vaccination—Trial 3 and 4

*Vibrio vulnificus* (ARS-1 Br-09) was grown at 28° C. in 500 ml TSB+NaCl for 24 h prior to adding 1% v/v formalin (24 h at 25° C.) to inactivate the cells. Following inactivation, 20 mL of the culture was centrifuged at 4000×g and 10 mL of the supernatant was discarded. The cell pellet was resuspended into the remaining 10 mL and was mixed with an equal volume of mineral oil. Following mixing, the suspension was emulsified via an 18 gauge micro-emulsifying needle. Fifty tilapia were immunized with the inactivated vaccine without adjuvant via IP injection of 100 μL per fish. A second group of fish (n=50) were IP injected with 100 μL per fish of the mineral oil adjuvanted vaccine. Cell counts of a sample taken prior to inactivation indicated $9 \times 10^6$ CFU was given to each fish. Two groups of fifty sham vaccinated fish were included and were IP injected with either 100 μL of sterile TSB+NaCl or 100 μL of TSB+NaCl emulsified with mineral oil.

At eighty-one dpv (Trial 3), duplicate groups of 10 randomly selected fish from the treatment and control groups were allocated to eight 57 L aquaria for the challenge. A single tank of 10 fish was included as mock infected controls. *Vibrio vulnificus* isolate CECT 4601 was grown in TSB+NaCl for 6 h at 28° C. to a cell density of $7.4 \times 10^8$ CFU/mL and then diluted 1:100 prior to challenge. Fish were challenged and the water was maintained as described for trial 1, with the exception that each fish received $7.4 \times 10^5$ CFU/fish. The challenge in Trial 4 was conducted at 88 dpv as described for Trial 3, with the exception that each fish was injected with $5.1 \times 10^5$ CFU/fish.

In Trial 3, tilapia vaccinated with the mineral oil adjuvanted *V. vulnificus* vaccine and challenged with a heterologous isolate showed significantly less ($p<0.05$) mortality than sham vaccinated with adjuvant group (Table 5). Relative percent survival was 73 for the mineral oil adjuvanted killed *V. vulnificus* vaccine. There was no significant difference between the mortality of fish vaccinated with the non-adjuvanted *V. vulnificus* vaccine and sham vaccinated group (Table 5). All dead fish from trial 3 were culture positive for *V. vulnificus*.

TABLE 5

Mean cumulative percent mortality (CPM) and relative percent survival of inactivated *V. vulnificus*-vaccinated, sex reversed hybrid tilapia challenged with the heterologous *V. vulnificus* isolate CECT 4601 (Trial 3).

| Treatment | N (replicate tanks of 10 fish each) | Mean CPM ± SE[1] | Relative % Survival |
|---|---|---|---|
| Sham vaccinated challenged* | 2 | $40 \pm 10^{a,b}$ | — |
| Sham vaccinated plus adjuvant challenged | 2 | $75 \pm 5^{a}$ | — |
| Vibrio vulnificus vaccinated challenged | 2 | $35 \pm 15^{a,b}$ | 12.5 |
| Adjuvanted Vibrio vulnificus vaccinated challenged | 2 | $20 \pm 10^{b}$ | 73.3 |
| Mock infected controls | 1 | 0.0 | NA |

*Challenged with $7.4 \times 10^5$ CFU/fish.
[1]Means with different superscript letters are significantly different at $p < 0.05$.

Results of Trial 4 showed that significantly lower mortality ($p<0.05$) occurred in both vaccinated groups than either of the sham vaccinated groups (Table 6) after challenge with the heterologous isolate (CECT 4601). Relative percent survival was 62.5 and 87.5% for the killed vaccine and adjuvanted vaccine treatments, respectively. Seven of the 8 dead sham vaccinated fish in each sham group were culture positive for *V. vulnificus*. One of 1 dead adjuvanted *V. vulnificus* vaccinated challenged fish and 2 of the 3 dead *V. vulnificus* vaccinated fish were culture positive for *V. vulnificus*.

TABLE 6

Mean cumulative percent mortality (CPM) and relative percent survival of inactivated *V. vulnificus*-vaccinated, sex reversed hybrid tilapia challenged with the heterologous *V. vulnificus* isolate CECT 4601 (Trial 4).

| Treatment | N (replicate tanks of 10 fish each) | Average Mortality ± SE[1] | Relative % Survival |
|---|---|---|---|
| Sham vaccinated challenged* | 2 | $40 \pm 0^{a}$ | — |
| Sham vaccinated plus adjuvant challenged | 2 | $40 \pm 10^{a}$ | — |

TABLE 6-continued

Mean cumulative percent mortality (CPM) and relative percent survival of inactivated *V. vulnificus*-vaccinated, sex reversed hybrid tilapia challenged with the heterologous *V. vulnificus* isolate CECT 4601 (Trial 4).

| Treatment | N (replicate tanks of 10 fish each) | Average Mortality ± SE[1] | Relative % Survival |
|---|---|---|---|
| *Vibrio vulnificus* vaccinated challenged | 2 | 15 ± 5[b] | 62.5 |
| Adjuvanted *Vibrio vulnificus* vaccinated challenged | 2 | 5 ± 5[b] | 87.5 |
| Mock infected controls | 1 | 0.0 | NA |

*Challenged with $5.1 \times 10^5$ CFU/fish.
[1]Means with different superscript letters are significantly different at $p < 0.05$.

Statistical Analysis: The t-test procedure of (SAS, Cary N.C., USA) was used to compare the mean percent mortality of the different vaccinated and sham vaccinated treatments (Trial 1 and 2). The same procedure was used to compare the mean agglutinating antibody titers of the vaccinated and sham vaccinated fish at different time points post immunization. The general linear models (GLM) procedure with Duncan's multiple range test was used to determine differences between treatments in Trial 3 and 4. Differences were considered significant at $p<0.05$.

*V. vulnificus* isolate ARS-1 Br-09 has been deposited with the USDA Agricultural Research Service Patent Culture Collection (National Center for Agricultural Utilization Research, 1815 N. University Street, Peoria, Ill., 61604, on Apr. 7, 2010, under accession number NRRL-B-50360, as a patent deposit under the Budapest Treaty on the International Recognition of the Deposit of Microorganisms for the Purposes of Patent Procedure.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A *Vibrio vulnificus* isolate from diseased fish which is biotype 1 and genotype 16S rRNA type B, vcg type C, and vvhA type 2, wherein said isolate of *V. vulnificus* is ARS-1Br-09 deposited under Accession Number NRRL-B-50360.

2. A vaccine composition for protecting fish against infection by vurulent straints of *V. vulnificus* comprising an immunologically effective amount of a *V. vulnificus* isolate wherein the isolate is biotype 1 and genotype 16S rRNA type B, vcg type C, and vvhA type 2; and a carrier, wherein said vaccine composition, after a single dose administration, elicits protective immunity in said fish against said virulent starins of *V. vulnificus*.

3. The vaccine composition claim 2 wherein the *V. vulnificus* isolate is NRRL-B-50360.

4. The vaccine composition claim 3 wherein the NRRL-B-50360 isolate is formalin-inactivated.

5. The vaccine composition of any one claims 2, 3 and 4 wherein said composition further comprises an adjuvant.

6. A method of providing protection to fish against infection by virulent strains of *V. vulnificus* comprising administering to said fish the vaccine composition of claim 2.

7. The method of claim 6 wherein said fish is selected from the group consisting of tilapia and other susceptible aquaculture fish species.

8. The method of claim 7 wherein said administering is by intraperitoneal injection or immersion of said fish in an aqueous medium containing said vaccine composition.

9. The method of claim 8 wherein said immunologically effective amount of said isolated *V. vulnificus* isolate in said vaccine is present in the aqueous medium at a concentration of about $1\times10^2$ CFU/ml to $1\times10^8$ CFU/ml.

10. The method of claim claim 8 wherein said immunologically effective amount of said isolated *V. vulnificus* isolate for intraperitoneal injection is about $1\times10^6$ CFU/fish.

11. A method of providing protection to fish against infection by virulent strains of *V. vulnificus* under conditions wherein fish are held in static salt water at concentrations of 1.5 g sea salt/L comprising administering to said fish the composition of claim 2.

* * * * *